United States Patent
Liu et al.

(10) Patent No.: US 10,471,381 B2
(45) Date of Patent: Nov. 12, 2019

(54) HIGH SELECTIVITY FACILITATED TRANSPORT MEMBRANES AND THEIR USE FOR OLEFIN/PARAFFIN SEPARATIONS

(71) Applicant: UOP LLC, Des Plaines, IL (US)

(72) Inventors: Chunqing Liu, Arlington Heights, IL (US); Carl W. Liskey, Chicago, IL (US); Howie Q. Tran, Skokie, IL (US); Nicole K. Karns, Chicago, IL (US)

( * ) Notice: Subject to any disclaimer, the term of this patent is extended or adjusted under 35 U.S.C. 154(b) by 45 days.

(21) Appl. No.: 15/598,168

(22) Filed: May 17, 2017

(65) Prior Publication Data

US 2017/0354918 A1 Dec. 14, 2017

Related U.S. Application Data

(60) Provisional application No. 62/348,112, filed on Jun. 9, 2016.

(51) Int. Cl.
| | | |
|---|---|---|
| B01D 69/10 | (2006.01) | |
| B01D 69/12 | (2006.01) | |
| B01D 53/22 | (2006.01) | |
| B01D 67/00 | (2006.01) | |
| B01D 71/08 | (2006.01) | |
| B01D 71/68 | (2006.01) | |
| C07C 7/144 | (2006.01) | |
| B01D 69/14 | (2006.01) | |

(52) U.S. Cl.
CPC ....... *B01D 53/228* (2013.01); *B01D 67/0088* (2013.01); *B01D 69/10* (2013.01); *B01D 69/12* (2013.01); *B01D 69/148* (2013.01); *B01D 71/08* (2013.01); *B01D 71/68* (2013.01); *C07C 7/144* (2013.01); *B01D 2256/24* (2013.01); *B01D 2325/36* (2013.01)

(58) Field of Classification Search
None
See application file for complete search history.

(56) References Cited

U.S. PATENT DOCUMENTS

| | | | |
|---|---|---|---|
| 3,133,132 A | 5/1964 | Sidney et al. | |
| 3,758,603 A | 9/1973 | Steigelmann et al. | |
| 5,198,316 A | 3/1993 | Wernet et al. | |
| 5,256,295 A | 10/1993 | Baker et al. | |
| 5,670,051 A | 9/1997 | Pinnau et al. | |
| 6,932,589 B2 | 8/2005 | Suzuki | |
| 7,048,846 B2 | 5/2006 | White et al. | |
| 7,125,935 B2 | 10/2006 | Andrews et al. | |
| 7,361,800 B2 | 4/2008 | Herrera et al. | |
| 7,803,275 B2 | 9/2010 | Partridge et al. | |
| 8,173,323 B2 | 5/2012 | An et al. | |
| 8,337,598 B2 | 12/2012 | Yates et al. | |
| 8,366,804 B2 | 2/2013 | Liu et al. | |
| 8,561,812 B2 | 10/2013 | Liu et al. | |
| 8,574,785 B2 | 11/2013 | Kim et al. | |
| 8,829,059 B2 | 9/2014 | Wynn et al. | |
| 8,912,288 B2 | 12/2014 | Liu et al. | |
| 9,017,451 B2 | 4/2015 | Wynn et al. | |
| 9,126,152 B2 | 9/2015 | Liu et al. | |
| 9,126,154 B2 | 9/2015 | Liu et al. | |
| 9,126,156 B2 | 9/2015 | Liu et al. | |
| 9,211,508 B2 | 12/2015 | Liu et al. | |
| 9,216,390 B2 | 12/2015 | Ho et al. | |
| 9,751,050 B2 | 9/2017 | Zhou et al. | |
| 10,258,929 B2 | 4/2019 | Liu et al. | |
| 2004/0154980 A1 | 8/2004 | Kim et al. | |
| 2004/0215045 A1 | 10/2004 | Herrera et al. | |
| 2006/0000778 A1 | 1/2006 | Childs et al. | |
| 2007/0190385 A1 | 8/2007 | Lee et al. | |
| 2008/0063917 A1 | 3/2008 | Yamashita et al. | |
| 2008/0268314 A1 | 10/2008 | Han et al. | |
| 2009/0277837 A1 | 11/2009 | Liu et al. | |
| 2010/0018926 A1 | 1/2010 | Liu et al. | |
| 2010/0147148 A1 | 6/2010 | Rabiei | |
| 2011/0094960 A1 | 4/2011 | Zhou et al. | |
| 2012/0031833 A1 | 2/2012 | Ho et al. | |
| 2012/0285881 A1 | 11/2012 | Jikihara et al. | |
| 2013/0255483 A1 | 10/2013 | Sanders et al. | |
| 2013/0299428 A1 | 11/2013 | Bikel et al. | |
| 2013/0233791 A1 | 12/2013 | Koo et al. | |
| 2014/0137734 A1 | 5/2014 | Liu et al. | |
| 2014/0290478 A1 | 10/2014 | Liu et al. | |
| 2015/0025293 A1 | 1/2015 | Feiring et al. | |
| 2015/0053079 A1 | 2/2015 | Koros et al. | |
| 2015/0068978 A1 | 3/2015 | Lando et al. | |
| 2015/0098872 A1 | 4/2015 | Kelly et al. | |
| 2016/0107127 A1 | 4/2016 | Lee et al. | |
| 2016/0177035 A1 | 6/2016 | Liu et al. | |
| 2016/0325229 A1 | 11/2016 | Zhou et al. | |

(Continued)

FOREIGN PATENT DOCUMENTS

| | | |
|---|---|---|
| CN | 103402614 A | 11/2013 |
| CN | 104275094 A | 1/2015 |
| EP | 458598 A2 | 11/1991 |
| EP | 1375459 A1 | 1/2004 |
| EP | 2545985 A1 | 1/2013 |
| EP | 2764908 A1 | 8/2014 |
| WO | 2009002747 A2 | 12/2008 |

OTHER PUBLICATIONS

PCT Search Report dated Sep. 14, 2017 for International Application No. PCT/US2017/036265.

(Continued)

*Primary Examiner* — Tam M Nguyen (57) ABSTRACT

This invention provides a new facilitated transport membrane comprising a relatively hydrophilic, very small pore, nanoporous support membrane, a hydrophilic polymer inside the very small nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the very small nanopores, a method of making this membrane, and the use of this membrane for olefin/paraffin separations, particularly for C3=/C3 and C2=/C2 separations.

13 Claims, 1 Drawing Sheet

(56) References Cited

U.S. PATENT DOCUMENTS

| | | | |
|---|---|---|---|
| 2017/0291143 A1 | 10/2017 | Zhou et al. | |
| 2017/0354918 A1 | 12/2017 | Liu et al. | |
| 2018/0001268 A1* | 1/2018 | Liu | B01D 67/0002 |
| 2018/0001277 A1 | 1/2018 | Liu et al. | |
| 2018/0154311 A1 | 6/2018 | Zhou et al. | |
| 2018/0333675 A1 | 11/2018 | Liu et al. | |
| 2018/0345230 A1 | 12/2018 | Karns et al. | |
| 2019/0060841 A1 | 2/2019 | Liu et al. | |
| 2019/0100479 A1* | 4/2019 | Liu | C07C 7/005 |
| 2019/0193021 A1* | 6/2019 | Rekoske | B01D 53/226 |

OTHER PUBLICATIONS

Chen, "Bioinspired fabrication of composite pervaporation membranes with high permeation flux and structural stability", Journal of Membrane Science 344 (2009) 136-143.

Ma, "High-flux thin-film nanofibrous composite ultrafiltration membranes containing cellulose barrier layer", J. Mater. Chem., 2010, 20, 4692-4704.

Wanichapichart, "Characteristics of polyethersulfone/chitosan composite membranes", Biophysics Unit, Membrane Science and Technology Research Center, Faculty of Science, Prince of Songkla University, Had Yai, Songkhla, Thailand 90112.

PCT Search Report dated Nov. 29, 2018 for PCT Appl. No. PCT/US2018/047547.

PCT Search Report dated Aug. 30, 2018 for PCT Appl. No. PCT/US2018/035004.

Kudinov, "Separation Characteristics of an Ejector Membrane-Sorption Hybrid System", Theoretical Foundations of Chemical Engineering, 2014, vol. 48, No. 6, 832-836, Pleiades Publishing, Ltd., 2014.

Riley, "Thin-Film Composite Membrane for Single-Stage Seawater Desalination by Reverse Osmosis", Applied Polymer Symposium No. 22, pp. 255-267 (1973).

Hess et al., Prpenelprpane separation with copolyimide membranes containing silver ions, Journal of Membrane Science, vol. 275, issue 1-2, 20 Apr. 2006, pp. 52-60.

PCT Search Report dated Sep. 14, 2017 for PCT Application No. PCT/US2017/038294.

Kang, "Novel Application of Partially Positively Charged Silver Nanoparticles for Facilitated Transport in Olefin/Paraffin Separation Membranes", Chem. Mater. 2008, 20, 1308-1311.

PCT Search Report dated Oct. 5, 2017 for PCT Appl. No. PCT/US2017/038307.

PCT Search Report dated Aug. 30, 2018 for PCT Appl. No. PCT/US2018/032251.

PCT Search Report dated Sep. 14, 2017 for PCT Appl. No. PCT/US2017/036265.

* cited by examiner

HIGH SELECTIVITY FACILITATED TRANSPORT MEMBRANES AND THEIR USE FOR OLEFIN/PARAFFIN SEPARATIONS

CROSS-REFERENCE TO RELATED APPLICATION

This application claims priority from Provisional Application No. 62/348,112 filed Jun. 9, 2016, the contents of which cited application are hereby incorporated by reference in its entirety.

BACKGROUND OF THE INVENTION

Over 170 Separex™ membrane systems have been installed in the world for gas separation applications such as for the removal of acid gases from natural gas, in enhanced oil recovery, and hydrogen purification. Two new Separex™ membranes (Flux+ and Select) have been commercialized recently by Honeywell UOP, Des Plaines, Ill. for carbon dioxide removal from natural gas. These Separex™ spiral wound membrane systems currently hold the membrane market leadership for natural gas upgrading. These membranes, however, do not have outstanding performance for olefin/paraffin separations. Development of new stable and very high selectivity membranes is critical for the future success of membranes for olefin/paraffin separation applications such as propylene/propane and ethylene/ethane separations.

Light olefins, such as propylene and ethylene, are produced as co-products from a variety of feedstocks in a number of different processes in the chemical, petrochemical, and petroleum refining industries. Various petrochemical streams contain olefins and other saturated hydrocarbons. Typically, these streams are from stream cracking units (ethylene production), catalytic cracking units (motor gasoline production), or the dehydrogenation of paraffins.

Currently, the separation of olefin and paraffin components is performed by cryogenic distillation, which is expensive and energy intensive due to the low relative volatilities of the components. Large capital expense and energy costs have created incentives for extensive research in this area of separations, and low energy-intensive membrane separations have been considered as an attractive alternative.

In principle, membrane-based technologies have the advantages of both low capital cost and high-energy efficiency compared to conventional separation methods for olefin/paraffin separations, such as propylene/propane and ethylene/ethane separations. Four main types of membranes have been reported for olefin/paraffin separations. These are facilitated transport membranes, polymer membranes, mixed matrix membranes, and inorganic membranes. Facilitated transport membranes, or ion exchange membranes, which sometimes use silver ions as a complexing agent, have very high olefin/paraffin separation selectivity. However, poor chemical stability, due to carrier poisoning or loss, high cost, and low flux, currently limit practical applications of facilitated transport membranes.

Separation of olefins from paraffins via conventional polymer membranes has not been commercially successful due to inadequate selectivities and permeabilities of the polymer membrane materials, as well as due to plasticization issues. Polymers that are more permeable are generally less selective than are less permeable polymers. A general trade-off has existed between permeability and selectivity (the so-called "polymer upper bound limit") for all kinds of separations, including olefin/paraffin separations. In recent years, substantial research effort has been directed to overcoming the limits imposed by this upper bound. Various polymers and techniques have been used, but without much success in terms of improving the membrane selectivity.

More efforts have been undertaken to develop metal ion incorporated, high olefin/paraffin selectivity facilitated transport membranes. The high selectivity for olefin/paraffin separations is achieved by the incorporation of metal ions such as silver (I) or copper (I) cations into the solid nonporous polymer matrix layer on top of the highly porous membrane support layer (so-called "fixed site carrier facilitated transport membrane") or directly into the pores of the highly porous support membrane (so-called "supported liquid facilitated transport membrane") that results in the formation of a reversible metal cation complex with the pi bond of olefins, whereas no interaction occurs between the metal cations and the paraffins. Addition of water, plasticizer, or humidification of the olefin/paraffin feed streams to either the fixed site carrier facilitated transport membranes or the supported liquid facilitated transport membranes is usually required to obtain reasonable olefin permeances and high olefin/paraffin selectivities. The performance of fixed site carrier facilitated transport membranes is much more stable than that of the supported liquid facilitated transport membranes and the fixed site carrier facilitated transport membranes are less sensitive to the loss of metal cation carriers than the supported liquid facilitated transport membranes.

Pinnau et al. disclosed a solid polymer electrolyte fixed site carrier facilitated transport membrane comprising silver tetrafluoroborate incorporated poly(ethylene oxide), see U.S. Pat. No. 5,670,051. Herrera et al. disclosed a process for the separation of olefin/paraffin mixtures using a silver cation-chelated chitosan fixed site carrier facilitated transport membrane, see U.S. Pat. No. 7,361,800. Herrera et al. disclosed the coating of a layer of chitosan on the surface of a microporous support membrane, wherein the support membrane is made from polyesters, polyamides, polyimides, polyvinylidene fluoride, polyacrylonitrile, polysulfones or polycarbonates.

Feiring et al. disclosed a new facilitated transport membrane comprising silver (I) cation exchanged fluorinated copolymer synthesized from a perfluorinated cyclic or cyclizable monomer and a strong acid highly fluorinated vinylether compound, see US 2015/0025293.

The composite facilitated transport membranes disclosed in the literature comprise an ultrafiltration or microfiltration membrane as the support membrane. The use of a relatively hydrophilic, nanoporous polymeric membrane such as polyethersulfone membrane as the support membrane for the preparation of fixed site carrier facilitated transport membranes for olefin/paraffin separations has not been reported in the literature. In particular, the use of a relatively hydrophilic, very small pore, nanoporous support membranes with an average pore diameter of less than 10 nm on the membrane skin layer surface for the preparation of fixed site carrier facilitated transport membranes has not been disclosed in the literature.

Development of new stable, high permeance, and high selectivity facilitated transport membranes is still required for the use of membranes for olefin/paraffin separations such as propylene/propane and ethylene/ethane separations.

SUMMARY OF THE INVENTION

This invention provides a new facilitated transport membrane comprising a relatively hydrophilic, very small pore, nanoporous support membrane, a hydrophilic polymer inside the very small nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the very small nanopores, a method of making this membrane, and the use of this membrane for olefin/paraffin separations, particularly for C3=/C3 and C2=/C2 separations.

The relatively hydrophilic, very small pore, nanoporous support membrane used for the preparation of the new facilitated transport membrane comprising a relatively hydrophilic, very small pore, nanoporous support membrane, a hydrophilic polymer inside the very small nanopores on the surface of the support membrane, a thin, nonporous, hydrophilic polymer layer coated on the surface of said support membrane, and metal salts incorporated in the hydrophilic polymer layer coated on the surface of the support membrane and said hydrophilic polymer inside the very small nanopores disclosed in the present invention comprises a relatively hydrophilic polymer selected from a group consisting of, but is not limited to, polyethersulfone (PES), a blend of PES and polyimide, cellulose acetate, cellulose triacetate, and a blend of cellulose acetate and cellulose triacetate. The relatively hydrophilic, very small pore, nanoporous support membrane described in the current invention has an average pore diameter of less than 10 nm on the membrane skin layer surface. The relatively hydrophilic, very small pore, nanoporous support membrane described in the current invention can be either asymmetric integrally skinned membrane or thin film composite (TFC) membrane with either flat sheet (spiral wound) or hollow fiber geometry.

The hydrophilic polymer inside the very small nanopores on the surface of the relatively hydrophilic, very small pore, nanoporous support membrane of the facilitated transport membrane described in the current invention can be selected from, but is not limited to, a group of hydrophilic polymers containing chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof.

The dried, relatively hydrophilic, very small pore, nanoporous support membrane comprising hydrophilic polymers inside the very small nanopores on the membrane surface described in the present invention has carbon dioxide permeance of 800-10,000 GPU and no carbon dioxide/methane selectivity at 50° C. under 30-100 psig 10% $CO_2$/90% $CH_4$ mixed gas feed pressure.

The thin, nonporous, hydrophilic polymer layer coated on the surface of said relatively hydrophilic, very small pore, nanoporous support membrane of the facilitated transport membrane described in the current invention comprises a hydrophilic polymer selected from, but is not limited to, a group of hydrophilic polymers containing chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof. The hydrophilic polymer in the thin, nonporous, hydrophilic polymer layer coated on the surface of said relatively hydrophilic, very small pore, nanoporous support membrane described in the current invention and the hydrophilic polymer inside the very small nanopores on the surface of said relatively hydrophilic, very small pore, nanoporous support membrane described in the current invention can be selected from the same hydrophilic polymer or different hydrophilic polymers. Preferably, the hydrophilic polymer in the thin, nonporous, hydrophilic polymer layer coated on the surface of said relatively hydrophilic, very small pore, nanoporous support membrane described in the current invention and the hydrophilic polymer inside the very small nanopores on the surface of said relatively hydrophilic, very small pore, nanoporous support membrane described in the current invention are selected from different hydrophilic polymers. As an example, the hydrophilic polymer in the thin, nonporous, hydrophilic polymer layer coated on the surface of said relatively hydrophilic, very small pore, nanoporous support membrane described in the current invention is chitosan and the hydrophilic polymer inside the very small nanopores on the surface of said relatively hydrophilic, very small pore, nanoporous support membrane described in the current invention is sodium alginate or sodium hyaluronate.

The metal salts incorporated in said hydrophilic polymer layer coated on the surface of said support membrane and said hydrophilic polymer inside the very small nanopores of the facilitated transport membrane described in the current invention are preferred to be selected from silver salts or copper salts, such as silver(I) nitrate or copper(I) chloride.

Olefin/paraffin permeation experimental results demonstrated that proper design of the new facilitated transport membranes described in the current invention is critical to achieve super high olefin/paraffin selectivity, high olefin permeance, and high performance stability for olefin/paraffin separations. The present invention discloses a new method of making the new facilitated transport membranes comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores. The method comprises: a) Preparation of a relatively hydrophilic, very small pore, nanoporous support membrane comprising hydrophilic polymers inside the very small nanopores on the skin layer surface of said support membrane via a phase inversion membrane casting or spinning fabrication process, the incorporation of the hydrophilic polymers into the very small nanopores on the skin layer surface of said support membrane is accomplished by the nipping of an aqueous solution of a hydrophilic polymer with a concentration in a range of 0.05 wt % to 5 wt % at the end of the membrane casting or spinning fabrication process or via the addition of the hydrophilic polymer to the gelation water tank during the membrane casting or spinning fabrication process; b) Coating a thin, nonporous, hydrophilic polymer layer on the skin layer surface of said relatively hydrophilic, very small pore, nanoporous support membrane comprising hydrophilic polymers inside the very small nanopores on the skin layer surface via any coating method such as dip-coating or meniscus coating method using an aqueous solution of the hydrophilic polymer with a concentration in a range of 0.2 wt % to 10 wt %; c) Preparation of the new facilitated transport membrane by soaking the thin, nonporous, hydrophilic polymer layer coated on the skin layer surface of said relatively hydrophilic, very small pore, nanoporous support membrane comprising hydrophilic polymers inside the very small nanopores on the skin layer surface in an aqueous solution of a metal salt such as silver nitrate ($AgNO_3$) with a concentration in a range of 0.2M to 10M for a certain time in a range from 1 min to 48 h.

The present invention provides a process to treat a gaseous feed stream comprising from 99 to 1 mole % of one or more C2-C8 olefins and from 1 to 99 mole % of one or more C1-C8 paraffins, said process comprising passing said gaseous feed stream to a feed side of a facilitated transport membrane comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores, so that not less than 80 mole % of the olefins in said feed stream pass through said facilitated transport membrane and recovering a permeate stream comprising not less than 90 mole % of olefin and not more than 10 mole % of paraffin.

DETAILED DESCRIPTION OF THE INVENTION

Figure 1:
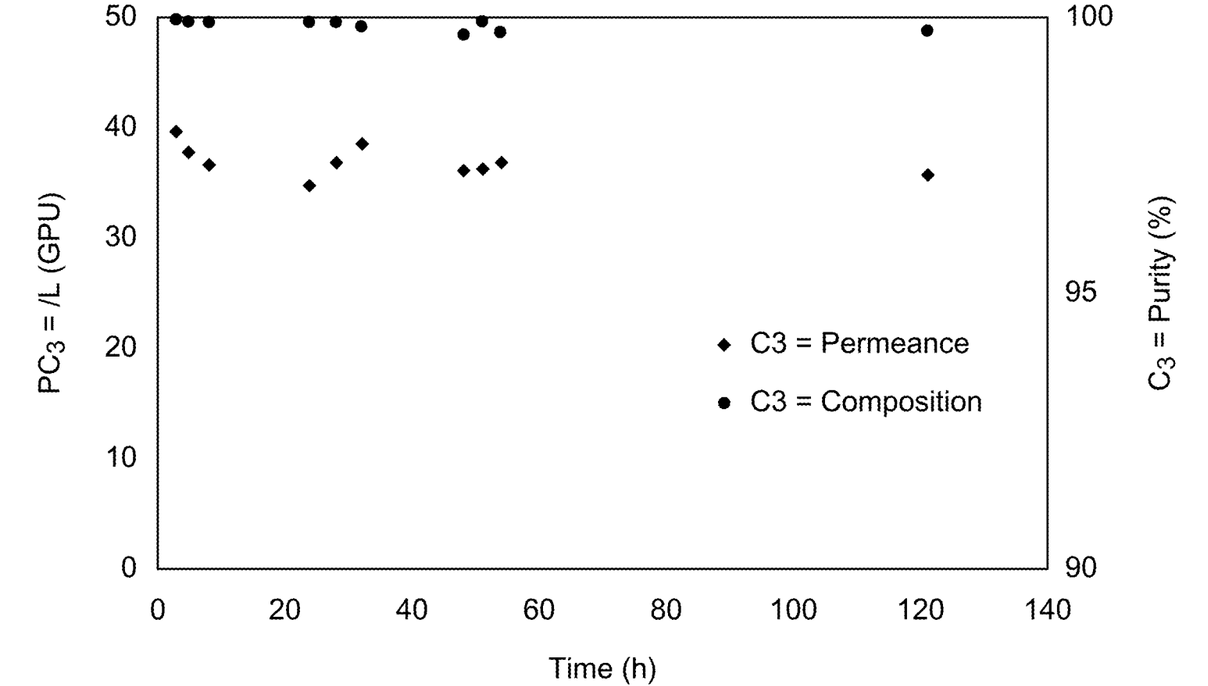
The FIGURE shows the change of permeance and purity of a UFTM-1 facilitated transport membrane over operating time.

Membrane technology has been of great interest for the separation of olefin/paraffin mixtures. However, despite significant research effort on olefin/paraffin separations by membrane technology, no commercial olefin/paraffin separation application using membranes has been reported so far.

This invention provides a new facilitated transport membrane comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores, a method of making this membrane, and the use of this membrane for olefin/paraffin separations, particularly for C3=/C3 and C2=/C2 separations.

The relatively hydrophilic, very small pore, nanoporous support membrane used for the preparation of the new facilitated transport membrane disclosed in the present invention comprises a relatively hydrophilic polymer selected from a group consisting of, but is not limited to, polyethersulfone (PES), a blend of PES and polyimide, cellulose acetate, cellulose triacetate, and a blend of cellulose acetate and cellulose triacetate. The relatively hydrophilic polymer described in the present invention is a water-insoluble polymer comprising ether groups or hydroxyl groups. The relatively hydrophilic, very small pore, nanoporous support membrane described in the current invention has an average pore diameter of less than 10 nm on the membrane skin layer surface. The relatively hydrophilic, very small pore, nanoporous support membrane described in the current invention can be either asymmetric integrally skinned membrane or thin film composite (TFC) membrane with either flat sheet (spiral wound) or hollow fiber geometry.

The hydrophilic polymer inside the very small nanopores on the skin layer surface of the relatively hydrophilic, very small pore, nanoporous support membrane of the facilitated transport membrane described in the current invention can be selected from, but is not limited to, a group of hydrophilic polymers containing chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof.

The thin, nonporous, hydrophilic polymer layer coated on the surface of said relatively hydrophilic, very small pore, nanoporous support membrane comprising hydrophilic polymers inside the very small nanopores on the skin layer surface of said support membrane described in the current invention comprises a hydrophilic polymer selected from, but is not limited to, a group of hydrophilic polymers containing chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof. The hydrophilic polymer in the thin, nonporous, hydrophilic polymer layer coated on the surface of said relatively hydrophilic, very small pore, nanoporous support membrane comprising hydrophilic polymers inside the very small nanopores on the skin layer surface of said support membrane described in the current invention and the hydrophilic polymer inside the very small nanopores on the skin layer surface of said support membrane described in the current invention can be selected from the same hydrophilic polymer or different hydrophilic polymers. Preferably, the hydrophilic polymer in the thin, nonporous, hydrophilic polymer layer coated on the surface of said relatively hydrophilic, very small pore, nanoporous support membrane comprising hydrophilic polymers inside the very small nanopores on the skin layer surface of said support membrane described in the current invention and the hydrophilic polymer inside the very small nanopores on the surface of said support membrane described in the current invention are selected from different hydrophilic polymers. As an example, the hydrophilic polymer in the thin, nonporous, hydrophilic polymer layer coated on the surface of said relatively hydrophilic, very small pore, nanoporous support membrane comprising hydrophilic polymers inside the very small nanopores on the skin layer surface of said support membrane described in the current invention is chitosan and the hydrophilic polymer inside the very small nanopores on the skin layer surface of said relatively hydrophilic, very small pore, nanoporous support membrane described in the current invention is sodium alginate or sodium hyaluronate.

The metal salts incorporated in said thin, nonporous, hydrophilic polymer layer coated on the surface of said support membrane and incorporated in said hydrophilic polymer inside the very small nanopores on the skin layer surface of said support membrane described in the current invention are preferred to be selected from silver salts or copper salts, such as silver(I) nitrate or copper(I) chloride.

The present invention teaches the incorporation of a hydrophilic polymer inside the very small nanopores on the surface of the relatively hydrophilic, very small pore, nanoporous support membrane for the preparation of the new facilitated transport membrane in the present invention. The hydrophilic polymer inside the very small nanopores on the surface of said relatively hydrophilic, very small pore, nanoporous support membrane reduces the pore size and stablizes the metal salts incorporated in said hydrophilic polymer inside the very small nanopores and the metal salts incorporated in said hydrophilic polymer layer coated on the surface of said support membrane described in the present invention via the interaction between the metal salt compounds and the hydrophilic functional groups such as hydroxyl or carboxylic acid groups on the hydrophilic polymer to prevent the loss of the metal salts from the facilitated transport membrane under certain applied feed pressure. In addition, the hydrophilic polymers inside the very small nanopores on the surface of said relatively hydrophilic, very small pore, nanoporous support membrane improves the adhesion between the relatively hydrophilic, very small pore, nanoporous support membrane and the thin, nonporous, hydrophilic polymer layer coated on the support membrane. The hydrophilic polymer can be incorporated into the very small nanopores on the surface of the relatively hydrophilic, very small pore, nanoporous support membrane in the present invention via nipping of an aqueous solution of a hydrophilic polymer at the end of a membrane casting or spinning fabrication process or via the addition of an aqueous solution of a hydrophilic polymer to the gelation water tank during the membrane casting or spinning fabrication process.

The current invention discloses the use of a relatively hydrophilic, very small pore, nanoporous support membrane for the preparation of the new facilitated transport membrane. The current invention further teaches the use of the relatively hydrophilic polymer such as PES for the preparation of said relatively hydrophilic, very small pore, nanoporous support membrane with an average pore diameter of less than 10 nm on the membrane skin layer surface for the preparation of the new facilitated transport membrane. The use of the relatively hydrophilic polymer such as PES, for the preparation of the very small pore, nanoporous support membrane in the present invention improves the interaction between the support membrane and the hydrophilic polymer inside the very small nanopores on the surface of said relatively hydrophilic, very small pore, nanoporous support membrane. The use of the relatively hydrophilic polymer such as PES for the preparation of the very small pore, nanoporous support membrane in the present invention also improved the adhesion between the relatively hydrophilic, very small pore, nanoporous support membrane and the thin, nonporous, hydrophilic polymer layer coated on the support membrane. The use of the very small pore, nanoporous support membrane comprising hydrophilic polymers inside the very small nanopores on the membrane surface for the preparation of the new facilitated transport membrane comprising metal salts in the present invention prevents the easy diffusion and transportation of the metal salt carriers from the hydrophilic polymer layer coated on the surface of the support membrane and the hydrophilic polymer inside the very small nanopores to the large pores underneath the very small nanopores of the support membrane, which will result in the loss of the metal salt carriers from the facilitated transport membrane under pressure. Therefore, the new facilitated transport membrane disclosed in the present invention provides high olefin/paraffin selectivity and high performance stability for olefin/paraffin separations. The dried, relatively hydrophilic, very small pore, nanoporous support membrane comprising hydrophilic polymers inside the very small nanopores on the membrane surface described in the present invention has carbon dioxide permeance of 800-10,000 GPU and no carbon dioxide/methane selectivity at 50° C. under 30-100 psig 10% $CO_2$/90% $CH_4$ mixed gas feed pressure.

The thin, nonporous, hydrophilic polymer layer coated on the skin layer surface of said support membrane in the present invention eliminates the defects on the new facilitated transport membrane and stabilizes the metal salts incorporated in said hydrophilic polymer layer coated on the skin layer surface of said support membrane via the interaction between the metal salt compounds and the hydrophilic functional groups such as hydroxyl or carboxylic acid groups on the hydrophilic polymer in said thin, nonporous, hydrophilic polymer layer. The thin, nonporous, hydrophilic polymer layer on the skin layer surface of said support membrane in the present invention can be formed via any coating method such as dip-coating or meniscus coating method.

The metal cations such as silver cations on the metal salts incorporated in the hydrophilic polymer layer coated on the surface of the support membrane and the hydrophilic polymer inside the very small nanopores on the skin layer surface of the support membrane of the facilitated transport membrane in the current invention form reversible metal cation complexes with the pi bonds of olefins, whereas no interactions occur between the metal cations and the paraffins in the new facilitated transport membrane described in the present invention. Therefore, the new facilitated transport membranes comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores described in the present invention can provide both high selectivity and high permeance for olefin/paraffin separations.

Olefin/paraffin permeation experimental results demonstrated that proper design of the new facilitated transport membranes described in the current invention is critical to achieve super high olefin/paraffin selectivity, high olefin permeance, and high performance stability for olefin/paraffin separations. The present invention discloses a new method of making the new facilitated transport membranes comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores. The method comprises: a) Preparation of a relatively hydrophilic, very small pore, nanoporous support membrane comprising hydrophilic polymers inside the very small nanopores on the skin layer surface of said support membrane via a phase inversion membrane casting or spinning fabrication process, the incorporation of the hydrophilic polymers into the very small nanopores on the skin layer surface of said support membrane is accomplished by the nipping of an aqueous solution of a hydrophilic polymer with a concentration in a range of 0.05 wt % to 5 wt % at the end of the membrane casting or spinning fabrication process or via the addition of the hydrophilic polymer to the gelation water tank during the membrane casting or spinning fabrication process; b) Coating a thin, nonporous, hydrophilic polymer layer on the skin layer surface of said relatively hydrophilic, very small pore, nanoporous support membrane comprising hydrophilic polymers inside the very small nanopores on the skin layer surface via any coating method such as dip-coating or meniscus coating method using an aqueous solution of the hydrophilic polymer with a concentration in a range of 0.2 wt % to 10 wt %; c) Preparation of the new facilitated transport membrane by soaking the thin, nonporous, hydrophilic polymer layer coated on the skin layer surface of said relatively hydrophilic, very small pore, nanoporous support membrane comprising hydrophilic polymers inside the very small nanopores on the skin layer surface in an aqueous solution of a metal salt such as silver nitrate ($AgNO_3$) with a concentration in a range of 0.2M to 10M for a certain time in a range from 1 min to 48 h. To prepare the relatively hydrophilic, very small pore, nanoporous support membrane in step a), a membrane casting or spinning dope comprising a relatively hydrophilic polymer such as PES, a solvent such as a mixture of N-methyl-2-pyrrolidone (NMP) and 1,3-dioxolane, a non-solvents such as an alcohol or a hydrocarbon, and an additive such as glycerol is used in the present invention. The addition of a hydrocarbon non-solvent such as n-hexane, n-heptane, n-decane or n-octane and a pore forming agent such as glycerol to the membrane casting or spinning dope formula is the key for the formation of very small nanopores with an average pore diameter of less than 10 nm on the membrane skin layer surface of the relatively hydrophilic, very small pore, nanoporous support membrane.

The new facilitated transport membranes comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores described in the present invention can be fabricated into any convenient form suitable for a desired olefin/paraffin application. For example, the membranes can be in the form of hollow fibers, tubes, flat sheets, and the like. The facilitated transport membrane in the present invention can be assembled in a separator in any suitable configuration for the form of the membrane and the separator may provide for co-current, counter-current, or cross-current flows of the feed on the retentate and permeate sides of the membrane. In one exemplary embodiment, the facilitated transport membrane comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores described in the present invention is in a spiral wound module that is in the form of flat sheet having a thickness from about 30 to about 400 μm. In another exemplary embodiment, the facilitated transport membrane comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores described in the present invention is in a hollow fiber module that is in the form of thousands, tens of thousands, hundreds of thousands, or more, of parallel, closely-packed hollow fibers or tubes. In one embodiment, each fiber has an outside diameter of from about 200 micrometers (μm) to about 700 millimeters (mm) and a wall thickness of from about 30 to about 200 μm. In operation, a feed contacts a first surface of said facilitated transport membrane described in the present invention, a permeate permeates said facilitated transport membrane described in the present invention and is removed therefrom, and a retentate, not having permeated said facilitated transport membrane described in the present invention, also is removed therefrom. In another embodiment, the facilitated transport membrane comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores described in the present invention can be in the form of flat sheet having a thickness in the range of from about 30 to about 400 μm.

The present invention provides a process for the separation of paraffin and olefin, such as, for example, in gaseous streams comprising from 99 to 1 mole % of one or more C2-C8 olefins and from 1 to 99 mole % of one or more C1-C8 paraffins produced from stream cracking, catalytic cracking, the dehydration of paraffins, and the like using the new facilitated transport membrane comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores in the present invention, said process comprising passing said gaseous feed stream to a feed side of a facilitated transport membrane comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores, so that not less than 80 mole % of the olefins in said feed stream pass through said facilitated transport membrane and recovering a permeate stream comprising not less than 90 mole % of olefin and not more than 10 mole % of paraffin. The process utilizes the new, stable, high selectivity facilitated transport membrane comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores described in the present invention that is highly permeable but also highly selective to olefin, thus permitting olefin to permeate the membrane at a much higher rate than the paraffin. The facilitated transport membrane comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores described in the present invention can take a variety of forms suitable for a particular application. For example, the membrane can be in the form of a flat sheet, hollow tube or fiber, and the like. In this regard, various embodiments of the process contemplated herein can be used to replace C2 and C3 splitters, as hybrid membrane/distillation units for olefin purification, for recovery of olefins from polypropylene vent streams or from fluid catalytic cracking (FCC) off-gas streams, or the like. The process can also be used for the production of polymer grade propylene, thus offering significant energy, capital, and operating cost savings compared to conventional distillation.

The olefin/paraffin separation process using the facilitated transport membrane comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores described in the present invention starts by contacting a first surface of the membrane with an olefin/paraffin feed. The olefin may comprise, for example, propylene or ethylene and the paraffin may comprise propane or ethane, respectively. The olefin/paraffin feed comprises a first concentration of olefin and a first concentration of paraffin depending on the application for which the membrane separation is used. For example, a propane dehydrogenation process typically provides a feed containing about 35 mass percent propylene, whereas a feed from an FCC unit generally contains about 75 mass percent propylene. The flow rate and temperature of the olefin/paraffin feed have those values that are suitable for a desired application. Next, a permeate is caused to flow through the membrane and from a second surface of the membrane. Because the stable high selectivity facilitated transport membrane comprising a relatively hydrophilic, very small pore, nanoporous support membrane, a hydrophilic polymer inside the very small nanopores on the skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores described in the present invention for olefin/paraffin separations is much more selective to the olefin than to the paraffin, the permeate has a concentration of olefin that is much higher than the concentration of the paraffin in the permeate. In one exemplary embodiment, the concentration of the olefin in the permeate is 99.5-99.9 mass percent. In addition, while some paraffin may permeate through the membrane, the permeate has a concentration of paraffin that is much less than the concentration of the paraffin in the feed. The permeate can then be removed from the second surface of the membrane. As the permeate passes through the membrane, a retentate or residue, which has not permeated the membrane, is removed from the first surface of the membrane. The retentate has a concentration of olefin that is much lower than the concentration of olefin in the feed and much lower than the concentration of the permeate. The retentate also has a concentration of paraffin that is higher than a concentration of paraffin that is in the feed.

EXAMPLES

The following examples are provided to illustrate one or more preferred embodiments of the invention, but are not limited embodiments thereof. Numerous variations can be made to the following examples that lie within the scope of the invention.

Example 1

UFTM-1 Facilitated Transport Membrane

A facilitated transport membrane (UFTM-1) with high propylene/propane selectivity was prepared from a relatively hydrophilic, very small pore, nanoporous support membrane containing a hydrophilic polymer within the very small nanopores on the membrane skin layer surface and another hydrophilic polymer coating on the membrane surface impregnated with silver nitrate. A relatively hydrophilic, very small pore, nanoporous, asymmetric polyethersulfone support membrane was prepared via the phase-inversion process. A membrane casting dope comprising, by approximate weight percentages, polyethersulfone (E6020P, BASF) 18-25%, N-methyl pyrrolidone 60-65%, 1,3-dioxolane 10-15%, glycerol 1-10% and n-decane 0.5-2% was cast on a nylon fabric then gelled by immersion in a 1° C. water bath for about 10 minutes, and then annealed in a hot water bath at 85° C. for about 5 minutes. A dilute aqueous solution of sodium alginate was applied via a nipping method onto the surface of the wet, relatively hydrophilic, very small pore, nanoporous, asymmetric polyethersulfone support membrane. The wet membrane comprising sodium alginate within the very small nanopores on the membrane skin layer surface was coated with a solution of chitosan dissolved in a dilute, aqueous acetic acid solution and then dried at 50° C. to form a thin, nonporous, chitosan layer on the surface of the membrane. The membrane was then treated with a basic sodium hydroxide solution, washed with water to form the polyethersulfone support membrane comprising alginic acid within the very small nanopores on the membrane skin layer surface and a thin, nonporous, chitosan layer on the surface of the membrane. The membrane was then impregnated with a silver nitrate aqueous solution (3M in $H_2O$). The wet membrane was then tested with a humidified (relative humidity 80-100%) propylene/propane ($C_3^=/C_3$) gas mixture (70% $C_3^=$/30% $C_3$) at 791 kPa (100 psig) and 50° C. The performance of UFTM-1 is shown in TABLE 1. UFTM-1 showed a propylene permeance of 39.8 GPU and a propylene/propane selectivity of >1000 corresponding to a permeate stream with a propylene purity of >99.9% after 3 h of testing. The UFTM-1 membrane was also tested with a 33% $C_3^=$/balance $C_3$ feed and the results were compared to those with 70% propylene in the feed. The comparison is shown in TABLE 2. The UFTM-1 membrane showed much higher propylene permeance and lower propylene/propane selectivity with a 33% $C_3^=$/balance $C_3$ feed.

Comparative Example 1

COMP-FTM-1 Facilitated Transport Membrane

A facilitated transport membrane (COMP-FTM-1) was prepared in the same method as EXAMPLE 1 except no sodium alginate nipping solution was applied. Without alginic acid within the very small nanopores on the skin layer surface of the polyethersulfone support membrane, the COMP-FTM-1 membrane showed a propylene permeance of 45.3 GPU and a low propylene/propane selectivity of 67.6 after 3 h of testing and the selectivity continued to decrease over time.

Example 2

UFTM-2 Facilitated Transport Membrane

A facilitated transport membrane (UFTM-2) was prepared in the same method as EXAMPLE 1 except a chitosan nipping solution was applied in addition to the chitosan coating layer. The membrane showed a propylene/propane selectivity of 152 after 3 h of testing and a similar permeance to UFTM-1 of 39.6 GPU.

Example 3

UFTM-3 Facilitated Transport Membrane

A facilitated transport membrane (UFTM-3) was prepared in the same method as EXAMPLE 1 except a sodium alginate solution was used to coat the surface of the support membrane following the sodium alginate nipping. The sodium alginate coated membrane was treated with a dilute acetic acid solution, washed with water and impregnated with silver nitrate.

TABLE 1

UFTM-1, UFTM-2, UFTM-3, and COMP-FTM-1 Facilitated Transport Membranes for Propylene/Propane Separation

| Membrane | Nipping Solution | Coating Solution | $P_{C3=}/L$ (GPU) | $\alpha_{C3=/C3}$ |
|---|---|---|---|---|
| UFTM-1 | sodium alginate | chitosan | 39.8 | 1160 |
| COMP-FTM-1 | none | chitosan | 45.3 | 67.6 |
| UFTM-2 | chitosan | chitosan | 39.6 | 152 |
| UFTM-3 | sodium alginate | sodium alginate | 27.0 | 596 |

The membranes were tested at 791 kPa (100 psig) 70% $C_3=$/30% $C_3$ gas pressure at 50° C. with a relative humidity of 80-100% and a retentate flow of 200 cc/min. Results reported after 3 h of testing. 1 GPU=1×10$^{-6}$ cm$^3$ (STP)/cm$^2$·s·cmHg

TABLE 2

Effect of Feed Composition on Propylene/Propane Separation Performance of UFTM-1 Facilitated Transport Membrane

| Membrane | Feed Composition | $P_{C3=}/L$ (GPU) | $\alpha_{C3=/C3}$ |
|---|---|---|---|
| UFTM-1 | 70% $C_3=$/30% $C_3$ | 39.8 | 1160 |
| UFTM-1 | 33% $C_3=$/67% $C_3$ | 77.1 | 490 |

The membranes were tested at 791 kPa (100 psig) pressure at 50° C. with a relative humidity of 80-100% and a retentate flow of 200 cc/min. Results reported after 3 h of testing. 1 GPU=1×10$^{-6}$ cm$^3$ (STP)/cm$^2$·s·cmHg Comparative Example 2

COMP-FTM-2 Facilitated Transport Membrane

A commercial microporous, ultrafiltration polysulfone support membrane (DSS-GR51PP) was coated with a solution of chitosan dissolved in a dilute, aqueous acetic acid solution and then dried at room temperature. The membrane was then treated with a basic sodium hydroxide solution, washed with water and impregnated with a silver nitrate aqueous solution (3M in H$_2$O). The wet COMP-FTM-2 membrane was then tested with a humidified (relative humidity 80-100%) propylene/propane ($C_3=$/$C_3$) gas mixture (70% $C_3=$) at 791 kPa (100 psig) and 50° C. The comparison to UFTM-1 is shown in TABLE 3. The membrane prepared on the microporous polysulfone support membrane showed very low permeance of <1 GPU, and the permeate flow was too low to measure the selectivity.

TABLE 3

Propylene/Propane Separation Performance of UFTM-1 and COMP-FTM-2 Facilitated Transport Membranes

| Membrane | Support | $P_{C3=}/L$ (GPU) | $\alpha_{C3=/C3}$ |
|---|---|---|---|
| UFTM-1 | nanoporous | 39.8 | 1156 |
| COMP-FTM-2 | microporous | <1 | —[1] |

The membranes were tested under 791 kPa (100 psig) pressure at 50° C. with a relative humidity of 80-100% and a retentate flow of 200 cc/min. Results reported after 3 h of testing. 1 GPU=1×10$^{-6}$ cm$^3$ (STP)/cm$^2$·s·cmHg [1] Too low to measure Comparative Example 3

While the COMP-FTM-1 and COMP-FTM-2 facilitated transport membranes without the hydrophilic polymer inside the pores on the membrane skin layer surface (i.e. no hydrophilic polymer was incorporated into the pores via the nipping method) showed a steady decrease in propylene permeance and propylene/propane selectivity over time presumably due to the loss of the silver carrier from the pores, the UFTM-1 facilitated transport membrane comprising alginic acid within the very small nanopores on the membrane skin layer surface of the relatively hydrophilic, very small pore, nanoporous, asymmetric polyethersulfone support membrane, a thin, nonporous, chitosan layer on the surface of the membrane, and silver(I) nitrate incorporated in the chitosan coating layer and alginic acid polymers inside the very small nanopores described in the present invention showed stability of >120 h with no noticeable decrease in propylene permeance or the purity of the propylene product. A purity of >99.7% propylene was maintained in the permeate stream with the propylene permeance of greater than 35 GPU. A plot of the propylene permeance and purity in the permeate over time is shown in the FIGURE.

Specific Embodiments

While the following is described in conjunction with specific embodiments, it will be understood that this description is intended to illustrate and not limit the scope of the preceding description and the appended claims.

A first embodiment of the invention is a process to treat a gaseous feed stream comprising from 99 to 1 mole % of one or more C2-C8 olefins and from 1 to 99 mole % of one or more C1-C8 paraffins, the process comprising passing the gaseous feed stream to a feed side of a facilitated transport membrane comprising a relatively hydrophilic, very small pore, nanoporous support membrane, a hydrophilic polymer inside the very small nanopores on a skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the very small nanopores so that not less than 80 mole % of the olefins in the feed stream pass through the membrane and recovering a permeate stream comprising not less than 90 mole % of olefin and not more than 10 mole % of paraffin. An embodiment of the invention is one, any or all of prior embodiments in this paragraph up through the first embodiment in this paragraph wherein the permeate stream is sent to an olefin/paraffin splitter to produce a product stream comprising more than 99 mole % olefin. An embodiment of the invention is one, any or all of prior embodiments in this paragraph up through the first embodiment in this paragraph wherein the permeate stream comprises more than 99.5 mole % olefin and is combined with the olefin product stream from an olefin/paraffin splitter.

A second embodiment of the invention is a facilitated transport membrane comprising a relatively hydrophilic, very small pore, nanoporous support membrane, a hydrophilic polymer inside the very small nanopores on a skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the very small nanopores. An embodiment of the invention is one, any or all of prior embodiments in this paragraph up through the second embodiment in this paragraph wherein the support membrane comprises a relatively hydrophilic polymer selected from the group consisting of polyethersulfone, a blend of polyethersulfone and polyimide, cellulose acetate, cellulose triacetate, and a blend of cellulose acetate and cellulose triacetate. An embodiment of the invention is one, any or all of prior embodiments in this paragraph up through the second embodiment in this paragraph wherein the support membrane comprises polyethersulfone. An embodiment of the invention is one, any or all of prior embodiments in this paragraph up through the second embodiment in this paragraph wherein the support membrane has an average pore diameter of less than 10 nm on the membrane skin layer surface. An embodiment of the invention is one, any or all of prior embodiments in this paragraph up through the second embodiment in this paragraph wherein the hydrophilic polymer inside the very small nanopores on the skin layer surface of the support membrane is selected from the group consisting of chitosan, sodium carboxylmethyl-chitosan, carboxylmethyl-chitosan, hyaluronic acid, sodium hyaluronate, carbopol, polycarbophil calcium, poly(acrylic acid), poly(methacrylic acid), sodium alginate, alginic acid, poly(vinyl alcohol), poly(ethylene oxide), poly(ethylene glycol), poly(vinylpyrrolidone), gelatin, carrageenan, sodium lignosulfonate, and mixtures thereof. An embodiment of the invention is one, any or all of prior embodiments in this paragraph up through the second embodiment in this paragraph wherein the hydrophilic polymer inside the very small nanopores on the skin layer surface of the support membrane is selected from the group consisting of chitosan, carboxylmethyl-chitosan, hyaluronic acid, and alginic acid. An embodiment of the invention is one, any or all of prior embodiments in this paragraph up through the second embodiment in this paragraph wherein the thin, nonporous, hydrophilic polymer layer coated on the surface of the support membrane comprises a hydrophilic polymer selected from the group consisting of chitosan, sodium carboxylmethyl-chitosan, carboxylmethyl-chitosan, hyaluronic acid, sodium hyaluronate, carbopol, polycarbophil calcium, poly(acrylic acid), poly(methacrylic acid), sodium alginate, alginic acid, poly(vinyl alcohol), poly(ethylene oxide), poly(ethylene glycol), poly(vinylpyrrolidone), gelatin, carrageenan, sodium lignosulfonate, and mixtures thereof. An embodiment of the invention is one, any or all of prior embodiments in this paragraph up through the second embodiment in this paragraph wherein the thin, nonporous, hydrophilic polymer layer coated on the surface of the support membrane comprises a hydrophilic polymer selected from the group consisting of chitosan, carboxylmethyl-chitosan, hyaluronic acid, and alginic acid. An embodiment of the invention is one, any or all of prior embodiments in this paragraph up through the second embodiment in this paragraph wherein the hydrophilic polymer in the thin, nonporous, hydrophilic polymer layer coated on the surface of the support membrane is the same as the hydrophilic polymer inside the very small nanopores on the skin layer surface of the support membrane. An embodiment of the invention is one, any or all of prior embodiments in this paragraph up through the second embodiment in this paragraph wherein the hydrophilic polymer in the thin, nonporous, hydrophilic polymer layer coated on the surface of the support membrane and the hydrophilic polymer inside the very small nanopores on the skin layer surface of the support membrane are chitosan. An embodiment of the invention is one, any or all of prior embodiments in this paragraph up through the second embodiment in this paragraph wherein the hydrophilic polymer in the thin, nonporous, hydrophilic polymer layer coated on the surface of the support membrane is different from the hydrophilic polymer inside the very small nanopores on the skin layer surface of the support membrane. An embodiment of the invention is one, any or all of prior embodiments in this paragraph up through the second embodiment in this paragraph wherein the hydrophilic polymer in the thin, nonporous, hydrophilic polymer layer coated on the surface of the support membrane is chitosan or hyaluronic acid and wherein the hydrophilic polymer inside the very small nanopores on the skin layer surface of the support membrane is alginic acid. An embodiment of the invention is one, any or all of prior embodiments in this paragraph up through the second embodiment in this paragraph wherein the metal salts incorporated in the hydrophilic polymer layer coated on the surface of the support membrane and the hydrophilic polymer inside the very small nanopores are silver salts or copper salts.

A third embodiment of the invention is a method of making a facilitated transport membrane comprising a relatively hydrophilic, very small pore, nanoporous support membrane, a hydrophilic polymer inside the very small nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the very small nanopores, comprising: (a) preparation of a relatively hydrophilic, very small pore, nanoporous support membrane comprising hydrophilic polymers inside the very small nanopores on the skin layer surface of the support membrane; (b) coating a thin, nonporous, hydrophilic polymer layer on the skin layer surface of the support membrane; and (c) preparation of the facilitated transport membrane by soaking the thin, nonporous, hydrophilic polymer layer on the skin layer surface of the support membrane in an aqueous metal salt solution. An embodiment of the invention is one, any or all of prior embodiments in this paragraph up through the third embodiment in this paragraph wherein the hydrophilic polymers are incorporated into the very small nanopores on the skin layer surface of the support membrane by nipping of an aqueous solution of the hydrophilic polymer on the support membrane at the end of the membrane casting or spinning fabrication process. An embodiment of the invention is one, any or all of prior embodiments in this paragraph up through the third embodiment in this paragraph wherein the hydrophilic polymers are incorporated into the very small nanopores on the skin layer surface of the support membrane by adding the hydrophilic polymer to the gelation water tank during the membrane casting or spinning fabrication process. An embodiment of the invention is one, any or all of prior embodiments in this paragraph up through the third embodiment in this paragraph wherein the thin, nonporous, hydrophilic polymer layer is formed by dip-coating an aqueous solution of the hydrophilic polymer on the skin layer surface of the support membrane. An embodiment of the invention is one, any or all of prior embodiments in this paragraph up through the third embodiment in this paragraph wherein the thin, nonporous, hydrophilic polymer layer is formed by meniscus coating an aqueous solution of the hydrophilic polymer on the skin layer surface of the support membrane.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A facilitated transport membrane, comprising a relatively hydrophilic, very small pore, nanoporous support membrane, a hydrophilic polymer inside the very small nanopores on a skin layer surface of said support membrane, a thin, nonporous, hydrophilic polymer layer coated on the surface of said support membrane, and metal salts incorporated in said hydrophilic polymer layer coated on the surface of said support membrane and said hydrophilic polymer inside the very small nanopores.

2. The membrane of claim 1 wherein said support membrane comprises a relatively hydrophilic polymer selected from the group consisting of polyethersulfone, a blend of polyethersulfone and polyimide, cellulose acetate, cellulose triacetate, and a blend of cellulose acetate and cellulose triacetate.

3. The membrane of claim 2 wherein said support membrane comprises polyethersulfone.

4. The membrane of claim 1 wherein said support membrane has an average pore diameter of less than 10 nm on the membrane skin layer surface.

5. The membrane of claim 1 wherein said hydrophilic polymer inside the very small nanopores on the skin layer surface of said support membrane is selected from the group consisting of chitosan, sodium carboxylmethyl-chitosan, carboxylmethyl-chitosan, hyaluronic acid, sodium hyaluronate, carbopol, polycarbophil calcium, poly(acrylic acid), poly(methacrylic acid), sodium alginate, alginic acid, poly(vinyl alcohol), poly(ethylene oxide), poly(ethylene glycol), poly(vinylpyrrolidone), gelatin, carrageenan, sodium lignosulfonate, and mixtures thereof.

6. The membrane of claim 5 wherein said hydrophilic polymer inside the very small nanopores on the skin layer surface of said support membrane is selected from the group consisting of chitosan, carboxylmethyl-chitosan, hyaluronic acid, and alginic acid.

7. The membrane of claim 1 wherein said thin, nonporous, hydrophilic polymer layer coated on the surface of said support membrane comprises a hydrophilic polymer selected from the group consisting of chitosan, sodium carboxylmethyl-chitosan, carboxylmethyl-chitosan, hyaluronic acid, sodium hyaluronate, carbopol, polycarbophil calcium, poly(acrylic acid), poly(methacrylic acid), sodium alginate, alginic acid, poly(vinyl alcohol), poly(ethylene oxide), poly(ethylene glycol), poly(vinylpyrrolidone), gelatin, carrageenan, sodium lignosulfonate, and mixtures thereof.

8. The membrane of claim 7 wherein said thin, nonporous, hydrophilic polymer layer coated on the surface of said support membrane comprises a hydrophilic polymer selected from the group consisting of chitosan, carboxylmethyl-chitosan, hyaluronic acid, and alginic acid.

9. The membrane of claim 8 wherein said hydrophilic polymer in said thin, nonporous, hydrophilic polymer layer coated on the surface of said support membrane is the same as said hydrphilic polymer inside the very small nanopores on the skin layer surface of said support membrane.

10. The membrane of claim 9 wherein said hydrophilic polymer in said thin, nonporous, hydrophilic polymer layer coated on the surface of said support membrane and said hydrphilic polymer inside the very small nanopores on the skin layer surface of said support membrane are chitosan.

11. The membrane of claim 1 wherein said hydrophilic polymer in said thin, nonporous, hydrophilic polymer layer coated on the surface of said support membrane is different from said hydrphilic polymer inside the very small nanopores on the skin layer surface of said support membrane.

12. The membrane of claim 11 wherein said hydrophilic polymer in said thin, nonporous, hydrophilic polymer layer coated on the surface of said support membrane is chitosan or hyaluronic acid and wherein said hydrphilic polymer inside the very small nanopores on the skin layer surface of said support membrane is alginic acid.

13. The membrane of claim 11 wherein said metal salts incorporated in said hydrophilic polymer layer coated on the surface of said support membrane and said hydrophilic polymer inside the very small nanopores are silver salts or copper salts.

* * * * *